United States Patent [19]

Suzuki et al.

[11] 4,107,162

[45] Aug. 15, 1978

[54] PROCESS FOR PREPARING $N_1$-(2'-FURANIDYL)-5-FLUOROURACIL

[75] Inventors: Nobuyuki Suzuki, Hyuga; Yukinari Kobayashi, Nobeoka; Yumiko Hiyoshi, Nobeoka; Seiji Takagi, Nobeoka; Takanori Sone, Nobeoka; Mikio Wakabayashi, Nobeoka; Tuneo Sowa, Nobeoka, all of Japan

[73] Assignee: Asahi Kasei Kogyo Kabushiki Kaisha, Osaka, Japan

[21] Appl. No.: 740,324

[22] Filed: Nov. 9, 1976

[30] Foreign Application Priority Data

Nov. 10, 1975 [JP] Japan ............................ 50-134805

[51] Int. Cl.$^2$ .......................................... C07D 239/54
[52] U.S. Cl. ..................................... 544/313; 544/229
[58] Field of Search ........................................ 260/260

[56] References Cited

U.S. PATENT DOCUMENTS

| 3,912,734 | 10/1975 | Giller et al. | 260/260 |
| 3,960,864 | 6/1976 | Townsend et al. | 260/260 |
| 4,039,546 | 8/1977 | Giller et al. | 260/260 |

Primary Examiner—Paul M. Coughlan, Jr.
Attorney, Agent, or Firm—Burgess, Dinklage & Sprung

[57] ABSTRACT

Process for preparing $N_1$-(2'-furanidyl)-5-fluorouracil having effective pharmacological activities such as anti-leukemia and anti-tumor activities comprising reacting 2,4-bis(trialkylsilyl)-5-fluorouracil with 2,3-dihydrofuran in the presence of a proton donor and a catalyst. Such process can be simply, easily conducted to give the desired product having a high purity in good yield.

9 Claims, No Drawings

PROCESS FOR PREPARING N₁-(2'-FURANIDYL)-5-FLUOROURACIL

This invention relates to a process for preparing N₁-(2'-furanidyl)-5-fluorouracil, and more particularly to a novel and useful process for preparing N₁-(2'-furanidyl)-5-fluorouracil which can be easily, simply carried out to give a high purity product in good yield.

N₁-(2'-furnanidyl)-5-fluorouracil shows effective pharmacological activities such as anti-leukemia and anti-tumor activities and has such excellent characteristics that it can be orally administered owing to its extremely lower side effects to digestive organs as compared with 5-fluorouracil and moreover it has a prolonged continuity of effect. This compound has thus attracted special attention in recent years.

As a method of preparing N₁-(2'-furanidyl)-5-fluorouracil or its 5-substituted derivatives, it has heretofore been proposed to react a mercury salt or a 2,4-bis(trimethylsilyl) derivative of the corresponding uracil to the desired product with 2-halogenotetrahydrofuran (Japanese Patent Application Publication No. 10510/1974). However, this known method has defects that since 2-halogenotetrahydrofuran used as the reactant is extremely unstable the reaction should be conducted at low temperatures and hence, handling is troublesome, and that 2-halogenotetrahydrofuran should be afresh prepared from 2,3-dihydrofuran each time it is used because it cannot be preserved. Further, the method employing as a starting material the mercury salts has many problems in the health control of workers and the treatment of the waste from the reaction. Therefore, this prior art method is unsuitable as an industrial method.

As a result of our intensive investigation with a view to developing a method for preparing N₁-(2'-furanidyl)-5-fluorouracil which can be easily, simply practiced, without the defects that the known methods have, to give a good yield, it has unexpectedly been found that the purpose can be attained by starting from 2,4-bis(trialkylsilyl)-5-fluorouracil represented by the general formula

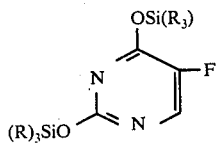

wherein R is a lower alkyl group, and 2,3-dihydrofuran represented by the formula

and conducting the reaction in the presence of a proton donor and a catalyst. The present invention has been made based on such novel finding.

Accordingly, it is an object of the present invention to provide a process for the preparation of N₁-(2'-furanidyl)-5-fluorouracil which can be simply, easily carried out to give a good yield.

It is another object of the present invention to provide a process of the kind described above, which can give a desired product of high purity.

The foregoing and other objects, features and advantages of the present invention will be apparent to those skilled in the art from the following detailed description and appended claims.

According to the present invention, there is provided a process for preparing N₁-(2'-furanidyl)-5-fluorouracil represented by the formula

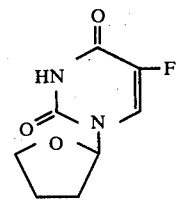

which comprises reacting a bis(trialkylsilyl) derivative of 5-fluorouracil represented by the general formula

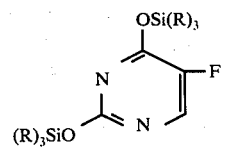

wherein R is a lower alkyl group, with 2,3-dihydrofuran in the presence of a proton donor and a catalyst.

The starting material of the general formula (II) is easily prepared by a known method, for example a method comprising reacting 5-fluorouracil with a silylating agent such as a hexaalkyldisilazane or a trialkylsilylchloride. The 2,4-bis(trialkylsilyl) derivative obtained may be used without purification but preferably after purification by reduced pressure distillation or the like.

2,3-Dihydrofuran to be used in the process of this invention is a well known compound and commercially available.

The amount of 2,3-dihydrofuran is not critical in the process of this invention, but usually ranges from 0.8 to 2.0 moles, preferably 1.0 to 1.5 moles per mole of the compound of the general formula (II). It is not economically advisable to use 2,3-dihydrofuran in an excessive amount over the amount required.

As catalysts to be used in the process of this invention, there can be mentioned Lewis acids, halogens and alkali metal iodides.

As specific examples of Lewis acids, though a wide variety of compounds capable of functioning as a Lewis acid can be used without specific limitation, there can be mentioned stannic chloride, aluminum chloride, titanium tetrachloride, silicon tetrachloride, antimony pentachloride and boron trifluoride. As halogens to be used in the process of this invention, there can be mentioned bromine and iodine, but especially, iodine gives a good result. As alkali metal iodides to be used in the process of this invention, there can be mentioned sodium iodide, potassium iodide and lithium iodide. The above-mentioned catalysts may be employed alone or in mixture.

The amount of the catalyst may vary widely in the range of 0.1 to 50 mole % based on the compound of the formula (II).

Since desired N₁-(2'-furanidyl)-5-fluorouracil is unstable to acids, it is preferable to use the catalyst in an amount as small as possible when the reaction is effected at high temperatures. When a halogen or an alkali metal iodide is used, it is preferable to avoid employment of a large amount of catalyst because the excessive amount of catalyst leads to increased coloration of the desired product. The adequate amount of Lewis acids to be used under given conditions can be easily determined by simple preparative experiments.

Since water contained in the solvent used in the process of this invention functions as a proton donor it is not always required to additionally employ a specific compound as the proton donor, but usually, the additional employment of a proton donor in an appropriate amount is advantageous to improve the yield of the desired product.

Any compound may be employed as the proton donor as far as it is liable to transfer the proton, but there may preferably be employed water, an alcohol such as methanol or butanol, an organic acid such as acetic acid or propionic acid, and the like. The above-mentioned proton donors may be employed alone or in mixture.

The adequate amount of a proton donor to be used in the process of this invention may vary depending on the water content of the solvent used, the reaction temperature, the kind of a catalyst used, the kind of proton donor to be used and the like, but may usually be in the range of 0.1 to 2.0 moles preferably 0.3 to 1.0 mole per mole of the compound of the general formula (II).

The reaction temperature employed in the process of this invention may be in the range of 10° to 200° C., preferably in the range of 50° to 170° C.

The reaction pressure may vary depending on the solvent employed as a reaction medium. Generally, there is required such a pressure as to maintain the reaction system in the state of liquid at the reaction temperature. In the process of this invention, there may usually be employed a pressure ranging from atmospheric up to about 10 atm.

The reaction time in the process of this invention may vary depending on the other reaction conditions, for example, the kind and amount of the catalyst used, the kind and amount of the proton source used and the reaction temperature. For example, when 5 mole % of stannic chloride as a catalyst and water as a proton donor is employed, the reaction time is preferably about 10 hours at room temperature, about 6 hours at 40° C. and about 30 minutes at 80° C. In the process of this invention, the reaction time may generally be in the range of 20 minutes to 15 hrs., usually 1 to 4 hrs.

In practicing the process of this invention, a solvent is not always necessary but the use of a solvent often gives a good result with respect to yield and coloration of the desired product. As solvents used, there can be mentioned polar aprotic solvents such as acetonitrile, dimethylformamide, dimethylsulfoxide and the like; esters such as ethyl acetate; halogenated hydrocarbons such as dichloroethane, dichloromethane and the like; and nitromethane etc.

The pattern of the desired product obtained by the process of this invention is extremely clear as compared with that of the product obtained by the conventional processes. Illustratively stated, almost no by-products are formed and there is obtained high purity $N_1$-(2'-furanidyl)-5-fluorouracil with an extremely small amount of the unreacted starting material of the general formula (II). In the conventional process, the reaction mixture usually contains by-products in an amount as high as 10 to 15%. Such by-products include, for example compounds of the following formulae:

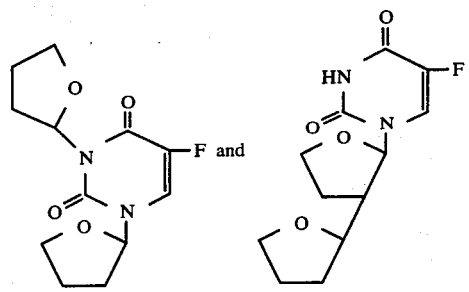

The above-mentioned by-products are very difficult to separate from the desired product. According to the process of the present invention, such by-products are formed in an amount as small as a few % or less. Therefore, a high purity product can be prepared.

The reaction mixture is, for example after neutralization, subjected to distillation under reduced pressure to distill off the solvent and then, water and an organic solvent such as dichloromethane, chloroform or the like is added to the residue. After the residue is completely dissolved, the organic solvent layer is separated whereby the desired $N_1$-(2'-furanidyl)-5-fluorouracil can be selectively extracted. On the other hand, the unreacted 5-fluorouracil copresent in the reaction system transfers into the water layer and can be easily separated and recovered. The desired product thus separated can be purified by the ordinary method such as recrystallization.

The following examples illustrate the invention in more detail but are not to be construed as limiting the scope thereof.

The formation rate (conversion) in Examples is calculated from the data of the analysis utilizing a high pressure filter paper electrophoresis under the following conditions.

| | |
|---|---|
| Buffer | boric acid buffer of pH 10.5 |
| Voltage | 4 KV |
| Electric current | 1 mA/cm width |
| Time | 70 – 80 minutes |
| Filter paper | Toyo filter paper No. 51 A (manufactured and sold by Toyo Roshi Co., Ltd., Japan) |

EXAMPLE 1

27.4 g. of 2,4-bis(trimethylsilyl)-5-fluorouracil and 7.7 g. of 2,3-dihydrofuran are dissolved in 70 ml. of acetonitrile, and 30 ml. of an acetonitrile solution containing 1.3 g. of anhydrous stannic chloride are added thereinto with cooling and stirring. 50 ml. of acetonitrile containing 1.3 ml. of water dissolved therein are then dropwise added over 15 minutes. After return to room temperature, the reaction is further effected with stirring at 40° C. for 5 hours. The reaction mixture is neutralized by adding 1 N aqueous ammonia with cooling and stirring (conversion 83%). After the non-dissolved substances are removed by filtration, the filtrate is concentrated and dried under reduced pressure. 100 ml. of water and 300 ml. of dichloromethane are added to the residue to completely dissolve the residue by stirring. The obtained dichloromethane layer is separated. The water layer is subjected to extraction twice with dichloromethane. The thus obtained extracts are combined with the separated dichloromethane layer and the combined extracts, after drying with anhydrous magnesium sulfate, are concentrated and dried. The obtained residue is dissolved in ethanol, and the non-dissolved substances are removed by filtration. The filtrate is subjected to recrystallization to give white crystals, followed by further recrystallization of the mother liquor. There are totally obtained 15.6 g. of $N_1$-(2'-furanidyl)-5-fluorouracil. Yield: 78% of theory, with respect to 2,4-bis(trimethylsilyl)-5-fluorouracil.

Melting point: 167° – 168° C. $\lambda_{max.}^{pH2}$: 272 m$\mu$($\epsilon$=8940)

Ultimate analysis: ($C_8H_9O_3N_2F$)

|  | C | H | N |
|---|---|---|---|
| Found (%): | 48.30 | 4.35 | 13.73 |
| Calcd. (%): | 48.00 | 4.53 | 14.00 |

EXAMPLE 2

Substantially the same procedures as described in Example 1 are repeated except that 2.1 ml. of methanol are used instead of 1.3 ml. of water and the reaction is conducted for 6 hours (conversion: 86%). 15.8 g. of $N_1$-(2'-furanidyl)-5-fluorouracil are obtained. Yield: 79%

Melting point: 167° – 169° C. $\lambda_{max.}^{pH2}$: 272 m$\mu$($\epsilon$=8940)

Ultimate analysis: ($C_8H_9O_3N_2F$)

|  | C | H | N |
|---|---|---|---|
| Found (%): | 48.20 | 4.39 | 14.12 |
| Calcd. (%): | 48.00 | 4.53 | 14.00 |

EXAMPLE 3

Substantially the same procedures as described in Example 1 are repeated except that 9.0 g. of t-butyl alcohol are used instead of 1.3 ml. of water (conversion: 86%). 14.0 g. of $N_1$-(2'-furanidyl)-5-fluorouracil are obtained. Yield: 70%

Melting point: 166° – 168° C. $\lambda_{max.}^{pH2}$: 272m$\mu$($\epsilon$=8940)

Ultimate analysis: ($C_8H_9O_3N_2F$)

|  | C | H | N |
|---|---|---|---|
| Found (%): | 48.02 | 4.49 | 13.89 |
| Calcd. (%): | 48.00 | 4.53 | 14.00 |

EXAMPLE 4

Substantially the same procedures as described in Example 1 are repeated except that 4 ml. of acetic acid are used instead of 1.3 ml. of water (conversion: 75%). 13.0 g. of $N_1$-(2'-furanidyl)-5-fluorouracil are obtained. Yield: 65%

Melting point: 167° 168° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 47.98 | 4.58 | 14.08 |
| Calcd. (%): | 48.00 | 4.53 | 14.00 |

EXAMPLE 5

Substantially the same procedures as described in Example 1 are repeated except that 1.0 ml. of water is used instead of 1.3 ml. of water and the reaction is conducted at 25° C. for 12 hours (conversion: 81%). 15.0 g. of $N_1$-(2'-furanidyl)-5-fluorouracil are obtained. Yield: 75%

Melting point: 167° – 168° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 48.20 | 4.39 | 14.27 |
| Calcd. (%): | 48.00 | 4.53 | 14.00 |

EXAMPLE 6

Substantially the same procedures as described in Example 4 are repeated except that 0.65 g. of anhydrous aluminum chloride is used instead of 1.3 g. of anhydrous stannic chloride (conversion: 83%). 15.2 g. of $N_1$-(2'-furanidyl)-5-fluorouracil are obtained. Yield: 76%

Melting point: 167° – 168° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 48.13 | 4.50 | 13.79 |
| Calcd. (%): | 48.00 | 4.53 | 14.00 |

EXAMPLE 7

Substantially the same procedures as described in Example 5 are repeated except that 0.65 g. of anhydrous aluminum chloride is used instead of 1.3 g. of anhydrous stannic chloride and the reaction is conducted for 18 hours (conversion: 70%). 12.6 g. of $N_1$-(2'-furanidyl)-5-fluorouracil are obtained. Yield: 63%

Melting point: 166° – 168° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 48.08 | 4.60 | 14.03 |
| Calcd. (%): | 48.00 | 4.53 | 14.00 |

EXAMPLE 8

Substantially the same procedures as described in Example 7 are repeated except that the reaction is conducted at 80° C. for 1 hour in an autoclave (conversion: 81%). 15.2 g. of $N_1$-(2'-furanidyl)-5-fluorouracil are obtained. Yield: 76%

Melting point: 167° – 169° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 47.83 | 4.60 | 14.13 |
| Calcd. (%): | 48.00 | 4.53 | 14.00 |

EXAMPLE 9

Substantially the same procedures as described in Example 1 are repeated except that 30 g. of 2,4-bis(triethylsilyl)-5-fluorouracil are used instead of 27.4 g. of 2,4-bis(trimethylsilyl)-5-fluorouracil (conversion: 82%).

15.0 g. of $N_1$-(2'-furanidyl)-5-fluorouracil are obtained. Yield: 75%

Melting point: 168° – 168.5° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 47.90 | 4.54 | 13.93 |
| Calcd. (%): | 48.00 | 4.53 | 14.00 |

EXAMPLE 10

Substantially the same procedures as described in Example 1 are repeated except that 2.1 g. of titanium tetrachloride are used instead of 1.3 g. of anhydrous stannic chloride (conversion: 58%). 9.8 g. of $N_1$-(2'-furanidyl)-5-fluorouracil are obtained. Yield: 49%

Melting point: 166° – 168° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 47.88 | 4.41 | 13.88 |
| Calcd. (%): | 48.00 | 4.53 | 14.00 |

EXAMPLE 11

Substantially the same procedures as described in Example 3 are repeated except that 1.0 g. of boron trifluoride is used instead of 1.3 g. of anhydrous stannic chloride (conversion: 61%). 9.8 g. of $N_1$-(2'-furanidyl)-5-fluorouracil are obtained. Yield: 49%

Melting point: 168° – 169° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 47.91 | 4.57 | 14.06 |
| Calcd. (%): | 48.00 | 4.53 | 14.00 |

EXAMPLE 12

Substantially the same procedures as described in Example 2 are repeated except that dichloromethane is used as a solvent instead of acetonitrile. 14.2 g. of $N_1$-(2'-furanidyl)-5-fluorouracil are obtained. Yield: 71%

Melting point: 166° – 167° C. $\lambda_{max.}^{pH2O}$ 272 m$\mu$ ($\epsilon$=8940)

Ultimate analysis: ($C_8H_9O_3N_2F$)

|  | C | H | N |
|---|---|---|---|
| Found (%): | 48.09 | 4.44 | 14.21 |
| Calcd. (%): | 48.00 | 4.53 | 14.00 |

EXAMPLE 13

Substantially the same procedures as described in Example 8 are repeated except that dimethylformamide is used as a solvent instead of acetonitrile (conversion: 72%). 12.6 g. of $N_1$-(2'-furanidyl)-5-fluorouracil are obtained. Yield: 63%

Melting point: 166° – 168° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 47.91 | 4.56 | 14.07 |
| Calcd. (%): | 48.00 | 4.53 | 14.00 |

EXAMPLE 14

Substantially the same procedures as described in Example 10 are repeated except that nitromethane is used as a solvent instead of acetonitrile (conversion: 56%). 9.8 g. of $N_1$-(2'-furanidyl)-5-fluorouracil are obtained. Yield: 49%

Melting point: 167° – 168° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 48.08 | 4.52 | 14.08 |
| Calcd. (%): | 48.00 | 4.53 | 14.00 |

EXAMPLE 15

27.4 g. of 2,4-bis(trimethylsilyl)-5-fluorouracil, 8 g. of 2,3-dihydrofuran and 1.3 g. of iodine are dissolved in 0.15 liter of acetonitrile containing 0.9 ml. of water dissolved therein, and stirred at room temperature for 10 hours. The acetonitrile is distilled off at a bath temperature of 40° C. under reduced pressure. The residue (conversion: 72%) is treated in the same manner as described in Example 1 to give 12.8 g. of $N_1$-(2'-furanidyl)-5-fluorouracil. Yield: 64%

Melting point: 166° – 168° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 48.05 | 4.37 | 14.17 |
| Calcd. (%): | 48.00 | 4.53 | 14.00 |

EXAMPLE 16

Substantially the same procedures are described in Example 15 are repeated except that the reaction mixture is stirred at 40° C. for 5 hours (conversion: 82%). 15 g. of $N_1$-(2'-furanidyl)-5-fluorouracil are obtained. Yield: 76%

Melting point: 167° – 169° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%): | 47.95 | 4.55 | 14.07 |
| Calcd. (%): | 48.00 | 4.53 | 14.00 |

EXAMPLE 17

Substantially the same procedures as described in Example 15 are repeated except that 0.13 g. of iodine is used instead of 1.3 g. of iodine and the reaction mixture is stirred at 80° C. for 1 hour (conversion: 88%). 16 g. of $N_1$-(2'-furanidyl)-5-fluorouracil are obtained. Yield: 80%

Melting point: 166° – 168° C. $\lambda_{max.}^{pH2}$: 272 m$\mu$ ($\epsilon$=8940)

Ultimate analysis: ($C_8H_9O_3N_2F$)

|  | C | H | N |
|---|---|---|---|
| Found (%) | 47.88 | 4.48 | 14.03 |
| Calcd. (%) | 48.00 | 4.53 | 14.00 |

EXAMPLE 18

Substantially the same procedures as described in Example 17 are repeated except that 4.8 ml. of t-butyl alcohol are used instead of 0.9 ml. of water (conversion: 84%). 15 g. of $N_1$-(2'-furanidyl)-5-fluorouracil are obtained. Yield: 75%

Melting point: 167° - 168° C. $\lambda_{max.}^{pH2}$: 272 mμ ($\epsilon = 8940$)

Ultimate analysis: ($C_8H_9O_3N_2F$)

|  | C | H | N |
|---|---|---|---|
| Found (%) | 47.91 | 4.49 | 14.05 |
| Calcd. (%) | 48.00 | 4.53 | 14.00 |

EXAMPLE 19

Substantially the same procedures as described in Example 15 are repeated except that 0.25 g. of iodine is used instead of 1.3 g. of iodine and the reaction mixture is stirred at 150° C. for 1 hour in an autoclave (conversion: 75%). 13 g. of $N_1$-(2'-furanidyl)-5-fluorouracil are obtained. Yield: 65%

Melting point: 167° - 169° C. $\lambda_{max.}^{pH2}$: 272 mμ ($\epsilon = 8940$)

Ultimate analysis: ($C_8H_9O_3N_2F$)

|  | C | H | N |
|---|---|---|---|
| Found (%) | 47.81 | 4.51 | 14.06 |
| Calcd. (%) | 48.00 | 4.53 | 14.00 |

EXAMPLE 20

Substantially the same procedures as described in Example 17 are repeated except that 0.08 g. of $N_1$-(2'-furanidyl)-5-fluorouracil are obtained. Yield: 64%

Melting point: 165° - 167° C. $\lambda_{max.}^{pH2}$: 272 mμ ($\epsilon = 8940$)

Ultimate analysis: ($C_8H_9O_3N_2F$)

|  | C | H | N |
|---|---|---|---|
| Found (%) | 48.03 | 4.50 | 14.11 |
| Calcd. (%) | 48.00 | 4.53 | 14.00 |

EXAMPLE 21

Substantially the same procedures as described in Example 20 are repeated except that 4.8 ml. of t-butyl alcohol are used instead of 0.9 ml. of water (conversion: 70%). 12.4 g. of $N_1$-(2'-furanidyl)-5-fluorouracil are obtained. Yield: 62%

Melting point: 166° - 168° C. $\lambda_{max.}^{pH2}$: 272 mμ ($\epsilon = 8940$)

Ultimate analysis: ($C_8H_9O_3N_2F$)

|  | C | H | N |
|---|---|---|---|
| Found (%) | 47.83 | 4.46 | 14.06 |
| Calcd. (%) | 48.00 | 4.53 | 14.00 |

EXAMPLE 22

27.4 g. of 2,4-bis(trimethylsilyl)-5-fluorouracil, 8 g. of 2,3-dihydrofuran and 0.75 g. of sodium iodide are dissolved in 0.15 liter of acetonitrile containing 0.9 ml. of water dissolved therein and stirred at 150° C. for 1 hour in an autoclave. The acetonitrile is distilled off under reduced pressure. The residue (conversion: 78%) is treated in the same manner as described in Example 1 to give 14 g. of $N_1$-(2'-furanidyl)-5-fluorouracil. Yield: 70%

Melting point: 167° - 168° C. $\lambda_{max.}^{pH2}$: 272 mμ ($\epsilon = 8940$)

Ultimate analysis: ($C_8H_9O_3N_2F$)

|  | C | H | N |
|---|---|---|---|
| Found (%) | 48.20 | 4.33 | 14.11 |
| Calcd. (%) | 48.00 | 4.53 | 14.00 |

EXAMPLE 23

Substantially the same procedures as described in Example 22 are repeated except that 4.8 ml. of t-butyl alcohol are used instead of 0.9 ml. of water (conversion: 72%). 12.5 g. of $N_1$-(2'-furanidyl)-5-fluorouracil are obtained. Yield: 62.5%

Melting point: 167° - 168° C. $\lambda_{max.}^{pH2}$: 272 mμ ($\epsilon = 8940$)

Ultimate analysis: ($C_8H_9O_3N_2F$)

|  | C | H | N |
|---|---|---|---|
| Found (%) | 47.36 | 4.37 | 14.00 |
| Calcd. (%) | 48.00 | 4.53 | 14.00 |

EXAMPLE 24

Substantially the same procedures as described in Example 22 are repeated except that 3 ml. of acetic acid are used instead of 0.9 ml. of water and the reaction mixture is neutralized by 1 N-sodium hydroxide solution after the completion of the reaction (conversion: 75%). 13.2 g. of $N_1$-(2'-furanidyl)-5-fluorouracil are obtained. Yield: 66%

Melting point: 166° - 168° C. $\lambda_{max.}^{pH2}$: 272 mμ ($\epsilon = 8940$)

Ultimate analysis: ($C_8H_9O_3N_2F$)

|  | C | H | N |
|---|---|---|---|
| Found (%) | 48.11 | 4.50 | 14.23 |
| Calcd. (%) | 48.00 | 4.53 | 14.00 |

EXAMPLE 25

Substantially the same procedures as described in Example 22 are repeated except that 0.83 g. of potassium iodide is used instead of 0.75 g. of sodium iodide (conversion: 76%). 13.2 g. of $N_1$-(2'-furanidyl)-5-fluorouracil are obtained. Yield: 66%

Melting point: 165° - 166° C. $\lambda_{max.}^{pH2}$: 272 mμ ($\epsilon = 8940$)

Ultimate analysis: ($C_8H_9O_3N_2F$)

|  | C | H | N |
|---|---|---|---|
| Found (%) | 48.17 | 4.33 | 14.06 |

-continued

|  | C | H | N |
|---|---|---|---|
| Calcd. (%) | 48.00 | 4.53 | 14.00 |

EXAMPLE 26

Substantially the same procedures as described in Example 22 are repeated except that 0.67 g. of lithium iodide is used instead of 0.75 g. of sodium iodide (conversion: 75%). 12.9 g. of $N_1$-(2'-furanidyl)-5-fluorouracil are obtained. Yield: 65%

Melting point: 165° - 168° C. $\lambda_{max.}^{pH2}$: 272 m$\mu$ ($\epsilon$ = 8940)

Ultimate analysis: ($C_8H_9O_3N_2F$)

|  | C | H | N |
|---|---|---|---|
| Found (%) | 47.88 | 4.50 | 14.03 |
| Calcd. (%) | 48.00 | 4.53 | 14.00 |

EXAMPLE 27

Substantially the same procedures as described in Example 17 are repeated except that 35.9 g. of 2,4-bis(-triethylsilyl)-5-fluorouracil are used instead of 27.4 g. of 2,4-bis(trimethylsilyl)-5-fluorouracil (conversion: 85%). 15.2 g. of $N_1$-(2'-furanidyl)-5-fluorouracil are obtained. Yield: 76%

Melting point: 168° - 168.5° C. $\lambda_{max.}^{pH2}$: 272 m$\mu$ ($\epsilon$ = 8940)

Ultimate analysis: ($C_8H_9O_3N_2F$)

|  | C | H | N |
|---|---|---|---|
| Found (%) | 48.12 | 4.40 | 14.11 |
| Calcd. (%) | 48.00 | 4.53 | 14.00 |

EXAMPLE 28

Substantially the same procedures as described in Example 22 are repeated except that 35.9 g. of 2,4-bis(-triethylsilyl)-5-fluorouracil are used instead of 27.4 g. of 2,4-bis(trimethylsilyl)-5-fluorouracil (conversion: 76%). 13.6 g. of $N_1$-(2'-furanidyl)-5-fluorouracil are obtained. Yield: 68%

Melting point: 166° - 168° C. $\lambda_{max.}^{pH2}$: 272 m$\mu$ ($\epsilon$ = 8940)

Ultimate analysis: ($C_8H_9O_3N_2F$)

|  |  |  |  |
|---|---|---|---|
| Found (%) | 47.93 | 4.59 | 14.21 |
| Calcd. (%) | 48.00 | 4.53 | 14.00 |

EXAMPLE 29

Substantially the same procedures as described in Example 19 are repeated except that dimethylformamide is used as a solvent instead of acetonitrile and the solvent is distilled off at 80° C. under reduced pressure (conversion: 63%). 10 g. of $N_1$-(2'-furanidyl)-5-fluorouracil are obtained. Yield: 50%

Melting point: 167° - 169° C. $\lambda_{max.}^{pH2}$: 272 m$\mu$ ($\epsilon$ = 8940)

Ultimate analysis: ($C_8H_9O_3N_2F$)

|  | C | H | N |
|---|---|---|---|
| Found (%) | 48.06 | 4.40 | 14.13 |

-continued

|  | C | H | N |
|---|---|---|---|
| Calcd. (%) | 48.00 | 4.53 | 14.00 |

EXAMPLE 30

Substantially the same procedures as described in Example 28 are repeated except that dimethylformamide is used as a solvent instead of acetonitrile and the solvent is distilled off under reduced pressure (conversion: 64%). 9.8 g. of $N_1$-(2'-furanidyl)-5-fluorouracil are obtained. Yield: 49%

Melting point: 167° - 169° C. $\lambda_{max.}^{pH2}$: 272 m$\mu$ ($\epsilon$ = 8940)

Ultimate analysis: ($C_8H_9O_3N_2F$)

|  | C | H | N |
|---|---|---|---|
| Found (%) | 47.90 | 4.52 | 14.01 |
| Calcd. (%) | 48.00 | 4.53 | 14.00 |

EXAMPLE 31

Substantially the same procedures as described in Example 1 are repeated except that 0.3 of anhydrous aluminum chloride, 0.2 g. of iodine and 0.2 g. of lithium iodide are used instead of 1.3 g. of anhydrous stannic chloride, and the reaction is conducted at 70° C. for 3.5 hours (conversion: 89%). 16.0 g. of $N_1$-(2'-furanidyl)-5-fluorouracil are obtained. Yield: 80%

Melting point: 167° - 167.5° C. $\lambda_{max.}^{pH2}$: 272 m$\mu$ ($\epsilon$ = 8940)

Ultimate analysis: ($C_8H_9O_3N_2F$)

|  | C | H | N |
|---|---|---|---|
| Found (%) | 48.07 | 4.47 | 14.11 |
| Calcd. (%) | 48.00 | 4.53 | 14.00 |

EXAMPLE 32

Substantially the same procedures as described in Example 1 are repeated except that 0.4 g. of anhydrous aluminum chloride and 0.4 g. of potassium iodide are used instead of 1.3 g. of anhydrous stannic chloride, and the reaction is conducted at 150° C. for 40 minutes in an autoclave (conversion: 81%). 15 g. of $N_1$-(2'-furanidyl)-5-fluorouracil are obtained. Yield: 76%

Melting point: 167° - 168° C. $\lambda_{max.}^{pH2}$: 272 m$\mu$ ($\epsilon$ = 8940)

Ultimate analysis: ($C_8H_9O_3N_2F$)

|  | C | H | N |
|---|---|---|---|
| Found (%) | 47.83 | 4.59 | 14.17 |
| Calcd. (%) | 48.00 | 4.53 | 14.00 |

EXAMPLE 33

Substantially the same procedures as described in Example 1 are repeated except that 0.6 g. of anhydrous stannic chloride and 1.3 g. of iodine are used instead of 1.3 g. of anhydrous stannic chloride, and the reaction is conducted at 50° C. for 4.5 hours (conversion: 82%). 15.2 g. of $N_1$-(2'-furanidyl)-5-fluorouracil are obtained. Yield: 76%

Melting point: 167° – 168° C. $\lambda_{max}^{pH2}$: 272 mµ ($\epsilon = 8940$)

Ultimate analysis: ($C_8H_9O_3N_2F$)

|  | C | H | N |
|---|---|---|---|
| Found (%) | 47.90 | 4.41 | 14.20 |
| Calcd. (%) | 48.00 | 4.53 | 14.00 |

EXAMPLE 34

Substantially the same procedures as described in Example 1 are repeated except that 50 ml. of acetonitrile containing 0.5 ml. of water and 1.6 ml. of methyl alcohol dissolved therein are used instead of 50 ml. of acetonitrile containing 1.3 ml. of water dissolved therein (conversion: 84%). 15.8 g. of $N_1$-(2'-furanidyl)-5-fluorouracil are obtained. Yield: 79%

Melting point: 165.5° – 167° C. $\lambda_{max}^{pH2}$: 272 mµ = 8940)

Ultimate analysis: ($C_8H_9O_3N_2F$)

|  | C | H | N |
|---|---|---|---|
| Found (%) | 48.03 | 4.50 | 14.21 |
| Calcd. (%) | 48.00 | 4.53 | 14.00 |

EXAMPLE 35

Substantially the same procedures as described in Example 1 are repeated except that 50 ml. of acetonitrile containing 0.5 ml. of water, 1.0 ml. of methyl alcohol and 1.1 ml. of acetic acid dissolved therein are used instead of 50 ml. of acetonitrile containing 1.3 ml. of water dissolved therein (conversion: 81%). 15.2 g. of $N_1$-(2'-furanidyl)-5-fluorouracil are obtained. Yield: 76%

Melting point: 168° – 169° C. $\lambda_{max}^{pH2}$: 272 mµ ($\epsilon = 8940$)

Ultimate analysis: ($C_8H_9O_3N_2F$)

|  | C | H | N |
|---|---|---|---|
| Found (%) | 48.14 | 4.50 | 14.13 |
| Calcd. (%) | 48.00 | 4.53 | 14.00 |

EXAMPLE 36

Substantially the same procedures as described in Example 31 are repeated except that 50 ml. of acetonitrile containing 0.5 ml. of water and 2.0 ml. of ethyl alcohol dissolved therein are used instead of 50 ml. of acetonitrile containing 1.3 ml. of water dissolved therein (conversion: 82%). 15 g. of $N_1$-(2'-furanidyl)-5-fluorouracil are obtained. Yield: 76%

Melting point: 167° – 167.5° C. $\lambda_{max}^{pH2}$: 272 mµ ($\epsilon = 8940$)

Ultimate analysis: ($C_8H_9O_3N_2F$)

|  | C | H | N |
|---|---|---|---|
| Found (%) | 48.06 | 4.49 | 14.08 |
| Calcd. (%) | 48.00 | 4.53 | 14.00 |

EXAMPLE 37

Substantially the same procedures as described in Example 31 are repeated except that 50 ml. of acetonitrile containing 0.5 ml. of water, 1.0 ml. of ethyl alcohol and 1.1 ml. of acetic acid dissolved therein are used instead of 50 ml. of acetonitrile containing 1.3 ml. of water dissolved therein (conversion: 78%). 14 g. of $N_1$-(2'-furanidyl)-5-fluorouracil are obtained. Yield: 70%

Melting point: 167° – 169° C. $\lambda_{max}^{pH2}$: 272 mµ ($\epsilon = 8940$)

Ultimate analysis: ($C_8H_9O_3N_2F$)

|  | C | H | N |
|---|---|---|---|
| Found (%) | 49.99 | 4.51 | 14.02 |
| Calcd. (%) | 48.00 | 4.53 | 14.00 |

The compound of the present invention may be effectively used substantially in the same manner as described in, for example, U.S. Pat. No. 3,635,946.

What is claimed is:

1. A process for preparing $N_1$-(2'-furanidyl)-5-fluorouracil of the formula

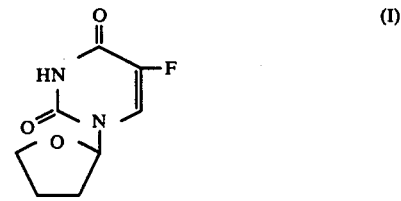

which comprises reacting a 2,4-bis(trialkylsilyl)-5-fluorouracil of the formula

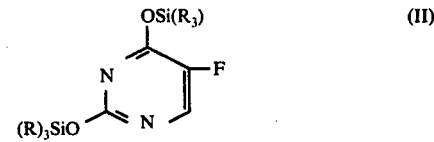

wherein R is a lower alkyl group, with 2,3-dihydrofuran in the presence of a catalyst selected from the group consisting of stannic chloride, aluminum chloride, titanium tetrachloride, silicon tetrachloride, antimony pentachloride, boron trifluoride, bromine, iodine, lithium iodide, sodium iodide, potassium iodide and mixtures thereof and a proton donor selected from the group consisting of water, an alcohol, an organic acid and mixtures thereof.

2. A process as claimed in Claim 1, wherein said lower alkyl group is a member selected from the group consisting of methyl and ethyl.

3. a process as claimed in claim 1, wherein 2,3-dihydrofuran is employed in an amount of 0.8 to 2.0 moles per mole of the compound of the formula (II).

4. A process as claimed in claim 1, wherein said catalyst is employed in an amount of 0.1 to 50 mole %, based on the compound of the formula (II).

5. A process as claimed in claim 1, wherein said proton donor is a member selected from the group consisting of methanol, ethanol, propanol, butanol and mixtures thereof.

6. A process as claimed in claim 1, wherein said proton donor is a member selected from the group consisting of acetic acid, propionic acid, methanesulfonic acid and mixtures thereof.

7. A process as claimed in claim 1, wherein said proton donor is employed in an amount of 0.1 to 2.0 moles per mole of the compound of the formula (II).

8. A process as claimed in claim 1, wherein the reaction is effected at a temperature of 10° to 200° C.

9. A process as claimed in claim 1, wherein the reaction is effected for 20 minutes to 15 hours.

* * * * *